United States Patent
Naya (10) Patent No.: US 7,307,731 B2
(45) Date of Patent: Dec. 11, 2007

(54) METHOD OF DETECTING TEST BODIES (75) Inventor: Masayuki Naya, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 408 days.

(21) Appl. No.: 11/029,023

(22) Filed: Jan. 5, 2005

(65) Prior Publication Data
US 2005/0168745 A1 Aug. 4, 2005

(30) Foreign Application Priority Data
Jan. 7, 2004 (JP) .............................. 2004-001552

(51) Int. Cl.
G01N 21/55 (2006.01)
(52) U.S. Cl. ..................................... 356/445
(58) Field of Classification Search ................. 356/445
See application file for complete search history.

(56) References Cited
U.S. PATENT DOCUMENTS
2003/0077839 A1* 4/2003 Takei ......................... 436/177

FOREIGN PATENT DOCUMENTS
| EP | 0 863 395 A2 | 9/1998 |
| EP | 0 965 835 A2 | 12/1999 |
| EP | 965835 A2 * | 12/1999 |
| EP | 1 445 601 A2 | 8/2004 |
| JP | 2000-356587 A | 12/2000 |
| JP | 2000356587 A * | 12/2000 |
| JP | 2003-268592 A | 9/2003 |
| JP | 2003268592 A * | 9/2003 |

OTHER PUBLICATIONS

Japanese Abstract No. 2003268592, dated Sep. 25, 2003.
"Surface Plasmon Resonance Biosensing with Colloidal Au Amplification", Michael J. Natan, Metal Nanoparticles, Synthesis, Characterization, and Applications, pp. 183-205.

* cited by examiner

Primary Examiner—Tarifur Chowdhury
Assistant Examiner—Jonathon D Cook
(74) Attorney, Agent, or Firm—Sughrue Mion Pllc.

(57) ABSTRACT

A fine structure body comprising first fine metal particles, which have head regions projected upwardly from a surface of a base body, is utilized. A substance capable of undergoing specific binding with a test body is fixed to the head regions of the first fine metal particles. Second fine metal particles, to which a substance capable of undergoing specific binding with the test body has been fixed, are dispersed in a sample liquid. The test body is detected from variation of a resonance wavelength of localized plasmon resonance, which variation occurs when the test body is adsorbed to the surface of the fine structure body by being sandwiched between the substance fixed to the first fine metal particle and the substance fixed to the second fine metal particle.

10 Claims, 4 Drawing Sheets

METHOD OF DETECTING TEST BODIES

BACKGROUND OF THE INVENTION

1. Field of the Invention

This invention relates to a method of detecting a test body with a sensor utilizing a localized plasmon resonance phenomenon.

2. Description of the Related Art

As sensors utilized for detection or identification of substances or for examination concerning molecular structures, sensors utilizing a localized plasmon resonance phenomenon have heretofore been known. The sensors utilizing the localized plasmon resonance phenomenon utilize a device having a structure, in which fine metal particles are secured in a layer-shaped form to a surface of a dielectric material, as a sensor chip. Also, the sensors are constituted of means for irradiating light to the layer of the fine metal particles of the sensor chip, and means for spectrophotometrically detecting the light, which has been reflected from the layer of the fine metal particles, and measuring the intensity of each of light components having different wavelengths.

In cases where light is irradiated to fine metal particles smaller than the wavelengths of the light, free electrons within the fine metal particles resonate with an electric field of a light component having a specific wavelength and begin to vibrate. The phenomenon described above is referred to as the localized plasmon resonance phenomenon. In cases where the electrons within the fine metal particles begin to vibrate, and the localized plasmon resonance is induced, strong electric fields occur around the fine metal particles, and the scattering and the absorption of the light component having the specific wavelength (hereinbelow referred to as the resonance wavelength) are caused to increase markedly.

In such cases, the resonance wavelength depends upon the refractive index of a substance, which is present around the fine metal particles. Specifically, in cases where the refractive index of the substance, which is present around the fine metal particles, is large, a resonance wavelength shifts to the long wavelength side, and the scattering and the absorption of the reflected light increase. Therefore, in cases where the irradiation of the light and the measurement of the intensity of the reflected light are performed in a state, in which a substance acting as a test body is capable of being adsorbed to the layer of the fine metal particles or accumulating on the layer of the fine metal particles, the test body is capable of being detected in accordance with a marked alteration in intensity of the reflected light. Also, the kind of the test body is capable of being specified in accordance with the wavelength, which is associated with the occurrence of the marked alteration in intensity of the reflected light. As the sensor chip for use in the sensors described above, for example, a sensor chip comprising a base body and a colloidal metal single-layer film, which is formed at a surface area of the base body, has heretofore been known. The sensor chip comprising the base body and the colloidal metal single-layer film, which is formed at the surface area of the base body, is described in, for example, Japanese Unexamined Patent Publication No. 2000-356587.

Also, as a technique for detecting a test body, which has been dispersed in a liquid, by use of a sensor chip of the type described above, there has been proposed a technique wherein, besides the fine metal particles having been fixed to the sensor chip, fine metal particles are bound to the side of the test body. (The proposed technique for detecting a test body is described in, for example, "Metal Nanoparticles, Synthesis, Characterization, and Applications," Daniel L. Feldheim, Colby A. Foss, Jr., MARCEL DEKKER Inc., pp. 183-205.) With the proposed technique for detecting a test body, at the time at which the test body has been adsorbed to the surface of the sensor chip, a fine metal particle on the side of the sensor chip and a fine metal particle on the side of the test body are located close to each other. The resonance wavelength of the localized plasmon resonance varies in accordance with the state, in which the fine metal particles are located close to each other. Therefore, in cases where the fine metal particles are bound to the side of the test body, the variation in resonance wavelength is capable of being found easily.

With the sensor chip disclosed in Japanese Unexamined Patent Publication No. 2000-356587, the problems are encountered in that the colloidal particles are apt to agglomerate, and therefore the sensor chip is difficult to produce, and in that the sizes of the fine metal particles are not uniform. As a technique for solving the problems described above, there has been proposed a technique, wherein regularly arrayed fine holes are formed previously on a base plate, fine metal particles are filled respectively in the fine holes, and a sensor chip of the type described above is thereby produced. (The technique for producing a sensor chip is described in, for example, Japanese Unexamined Patent Publication No. 2003-268592.)

The fine structure body disclosed in Japanese Unexamined Patent Publication No. 2003-268592 has the advantages over the sensor chip disclosed in Japanese Unexamined Patent Publication No. 2000-356587 in that the fine metal particles having uniform size are arrayed regularly, and in that reliable measurement results are capable of being obtained. However, with the fine structure body disclosed in Japanese Unexamined Patent Publication No. 2003-268592, wherein each of the fine metal particles is located in the interior of one of the fine holes, in cases where the technique for detecting a test body described in the aforesaid literature entitled "Metal Nanoparticles, Synthesis, Characterization, and Applications" is to be utilized, the problems are encountered in that it is difficult for a fine metal particle on the side of the sensor chip and a fine metal particle on the side of the test body to be located close to each other. Specifically, for certain types of sensing techniques, it often occurs that the fine structure body disclosed in Japanese Unexamined Patent Publication No. 2000-356587 is more appropriate than the fine structure body disclosed in Japanese Unexamined Patent Publication No. 2003-268592.

SUMMARY OF THE INVENTION

The primary object of the present invention is to provide a method of detecting a test body, wherein both the effect of a state, in which a fine metal particle on the side of a sensor chip and a fine metal particle on the side of the test body are located close to each other, and the effect of a state, in which fine metal particles having uniform size are arrayed regularly, are capable of being obtained.

Another object of the present invention is to provide a method of detecting a test body, wherein a sensing operation is capable of being performed with a high sensitivity.

The present invention provides a method of detecting a test body contained in a liquid, comprising the steps of:

i) obtaining a fine structure body comprising a base body, which has a plurality of fine holes distributed and formed in one surface, and first fine metal particles, each of which has a size such that localized plasmon resonance is capable of being induced, and each of which is located in one of the fine holes of the base body such that a head region of each of the first fine metal particles is projected to a side more upward than the surface of the base body, ii) locating the fine structure body in the liquid and in a state, in which a specific binding substance capable of undergoing specific binding with the test body has been fixed to the head region of each of the first fine metal particles, iii) dispersing a plurality of second fine metal particles, each of which has a size such that the localized plasmon resonance is capable of being induced, in the liquid and in a state, in which a specific binding substance capable of undergoing specific binding with the test body has been fixed to each of the second fine metal particles, iv) irradiating light to the surface of the fine structure body, from which surface the head regions of the first fine metal particles are projected, v) measuring an intensity of the light, which has been reflected from the surface of the fine structure body, or the light, which has passed through the fine structure body, and vi) detecting the test body, which is contained in the liquid, in accordance with the thus measured light intensity.

Specifically, in the method of detecting a test body in accordance with the present invention, firstly, the fine structure body (i.e., the sensor chip) is prepared. The fine structure body comprises the base body, which has the plurality of the fine holes distributed and formed in the one surface. The fine structure body also comprises the fine metal particles (i.e., the first fine metal particles), each of which has the size such that the localized plasmon resonance is capable of being induced, and each of which is located in one of the fine holes of the base body. The fine structure body is located in a sample liquid, which has the possibility of containing the test body.

Each of the first fine metal particles is located in one of the fine holes of the base body such that the head region of each of the first fine metal particles is projected to the side more upward than the surface of the base body. The hole diameter of each of the fine holes should preferably be at most 200 nm. The depth of each of the fine holes should preferably be at most 100 nm. Also, the variation of the hole diameters of the fine holes should preferably be at most 15%. The diameter of each of the head regions of the first fine metal particles should preferably be at most 200 nm. The first fine metal particles should preferably be constituted of a material selected from the group consisting of gold, silver, aluminum, and copper.

The fine structure body is located in the liquid and in the state, in which the specific binding substance capable of undergoing specific binding with the test body has been fixed to the head region of each of the first fine metal particles.

Further, the plurality of the fine metal particles (i.e., the second fine metal particles), each of which has the size such that the localized plasmon resonance is capable of being induced, are dispersed in the liquid and in the state, in which the specific binding substance capable of undergoing specific binding with the test body has been fixed to each of the second fine metal particles, such that the test body contained in the liquid is capable of undergoing the specific binding with the specific binding substance having been fixed to each of the second fine metal particles. The second fine metal particles should preferably be constituted of a material selected from the group consisting of gold, silver, aluminum, and copper.

In the state described above, the light is irradiated to the surface of the fine structure body, from which surface the head regions of the first fine metal particles are projected. Also, the intensity of the light, which has been reflected from the surface of the fine structure body, or the light, which has passed through the fine structure body, is measured. In cases where the test body is contained in the liquid, the test body is adsorbed to the surface of the fine structure body, such that the test body is sandwiched between the specific binding substance, which has been fixed to head region of each of the first fine metal particles, and the specific binding substance, which has been fixed to each of the second fine metal particles. At this time, the first fine metal particle and the second fine metal particle are located close to each other, and therefore the resonance wavelength of the localized plasmon resonance varies. Accordingly, the test body, which is contained in the liquid, is capable of being detected in accordance with the thus measured light intensity.

The method of detecting a test body in accordance with the present invention should preferably be modified such that the fine structure body comprises an alumina layer acting as the base body, which alumina layer has been formed with anodic oxidation of a material containing aluminum as a principal constituent, and the first fine metal particles, each of which is located in one of the fine holes of the alumina layer. The fine structure body having the structure described above is capable of being produced comparatively easily. Also, the fine structure body having the structure described above has little variation of the hole diameters of the fine holes and has a uniform surface structure. Therefore, with the fine structure body having the structure described above, reliable results are capable of being obtained from the measurement of the intensity of the light, which has been reflected from the surface of the fine structure body, or the light, which has passed through the fine structure body.

Also, the method of detecting a test body in accordance with the present invention should preferably be modified such that the fine structure body further comprises a thin metal film formed on areas of the surface of the base body, which areas are located around each of the fine holes of the base body. Further, the method of detecting a test body in accordance with the present invention should preferably be modified such that a diameter of each of the head regions of the first fine metal particles of the fine structure body is larger than the hole diameter of each of the fine holes of the fine structure body. With each of the aforesaid modifications of the method of detecting a test body in accordance with the present invention, the test body is capable of being detected with an enhanced sensitivity.

With the method of detecting a test body in accordance with the present invention, wherein the fine structure body having the uniform surface structure is employed, reliable measurement results are capable of being obtained. Also, in cases where the test body has been adsorbed to the surface of the fine structure body, the first fine metal particle and the second fine metal particle are capable of being located sufficiently close to each other, and the resonance wavelength of the localized plasmon resonance is capable of varying markedly. Therefore, the test body contained in the liquid is capable of being detected with a high sensitivity.

With the method of detecting a test body in accordance with the present invention, wherein the fine holes are formed with the anodic oxidation of the material containing aluminum as a principal constituent, the fine structure body having the uniform structure is capable of being obtained comparatively easily, and the sensing operation is capable of being performed with a high sensitivity.

The method of detecting a test body in accordance with the present invention may be modified such that the fine structure body further comprises the thin metal film formed on the areas of the surface of the base body, which areas are located around each of the fine holes of the base body. Further, the method of detecting a test body in accordance with the present invention may be modified such that the diameter of each of the head regions of the first fine metal particles of the fine structure body is larger than the hole diameter of each of the fine holes of the fine structure body. With each of the aforesaid modifications of the method of detecting a test body in accordance with the present invention, the sensitivity of the sensor is capable of being enhanced even further.

DESCRIPTION OF THE PREFERRED EMBODIMENTS

The present invention will hereinbelow be described in further detail with reference to the accompanying drawings.

Figure 1:
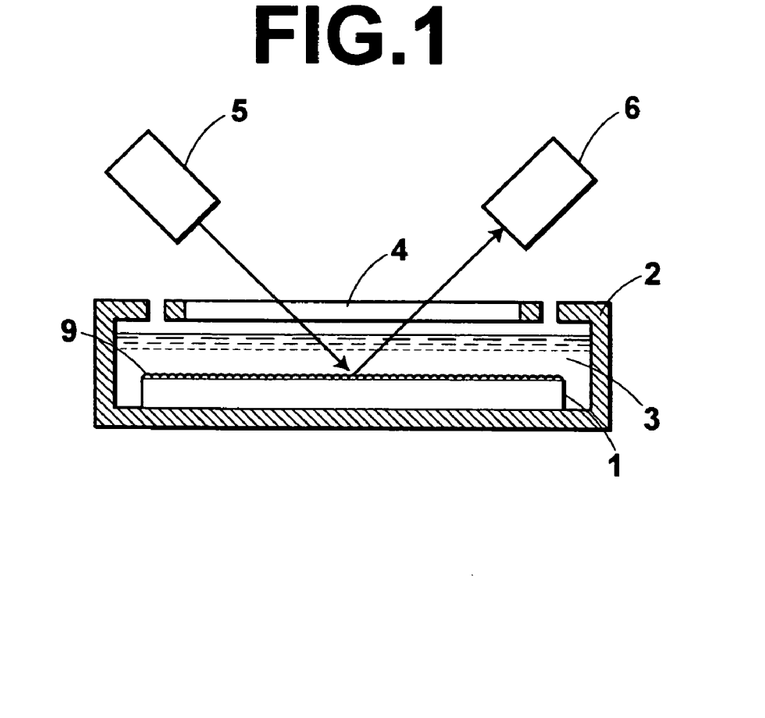
FIG. 1 is a schematic side view showing a reflection type of sensor, which is employed for detection of a test body in an embodiment of the method of detecting a test body in accordance with the present invention.

FIG. 1 is a schematic side view showing a reflection type of sensor, which is employed for detection of a test body in an embodiment of the method of detecting a test body in accordance with the present invention. As illustrated in FIG. 1, the sensor comprises a vessel 2 having a transparent window 4. The sensor also comprises a sensor chip 1, which is secured to the inside bottom surface of the vessel 2. The sensor further comprises a white light source 5 for irradiating white light 23 toward the sensor chip 1 having been secured to the inside bottom surface of the vessel 2. The sensor still further comprises a spectrophotometer 6 for spectrophotometrically detecting the light, which has been reflected from the surface of the sensor chip 1, and obtaining a spectrum of the reflected light. The spectrophotometer 6 thus detects a variation of the resonance wavelength of the localized plasmon resonance. A plurality of first fine gold particles 9, 9, . . . are arrayed on the surface of the sensor chip 1, to which surface the light is irradiated.

Figure 2:
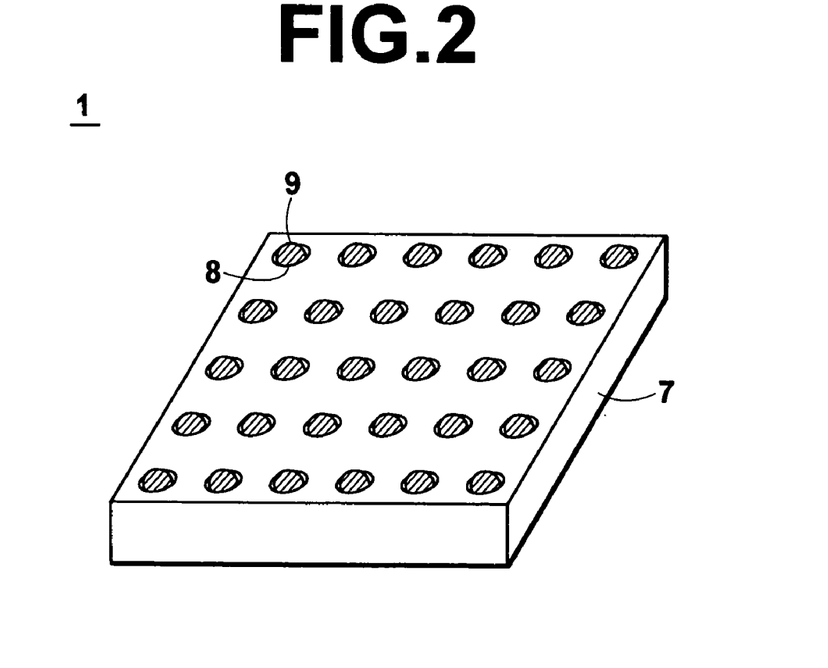
FIG. 2 is a perspective view showing an example of a structure of a sensor chip.

FIG. 2 is a perspective view showing the structure of the sensor chip 1. As illustrated in FIG. 2, the sensor chip 1 comprises a base body 7 having fine holes 8, 8, . . . distributed and formed on the surface. The sensor chip 1 also comprises the first fine gold particles 9, 9, . . . , each of which is located in one of the fine holes 8, 8, . . . . The hole diameter of each of the fine holes 8, 8, . . . is approximately 200 nm. The depth of each of the fine holes 8, 8, . . . is approximately 100 nm, i.e. approximately one half of the hole diameter of each of the fine holes 8, 8, . . . . The variation of the hole diameters of the fine holes 8, 8, . . . is at most 15%. The surface of the sensor chip 1 has a uniform structure. The particle diameter of each of the first fine gold particles 9, 9, . . . is slightly smaller than the hole diameter of each of the fine holes 8, 8, . . . and is approximately 200 nm. The particle diameter of each of the first fine gold particles 9, 9, . . . is larger than the depth of each of the fine holes 8, 8, . . . . Therefore, as illustrated in FIG. 2, part (i.e., the head region) of each of the first fine gold particles 9, 9, . . . is projected to the side more upward than the surface of the base body 7.

The sensor chip 1 may be produced with one of various processes. By way of example, how the sensor chip 1 is produced with a process, wherein an aluminum base body is employed, will be described hereinbelow. FIGS. 3A, 3B, 3C, and 3D are explanatory views showing the process for producing the sensor chip, wherein the aluminum base body is employed. Each of FIGS. 3A, 3B, 3C, and 3D shows part of cross-section of the sensor chip material for constituting the sensor chip 1.

Figure 3A:
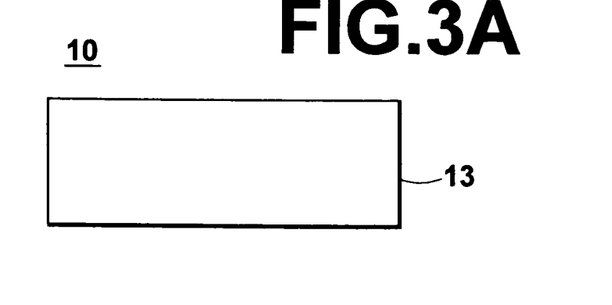
FIGS. 3A, 3B, 3C, and 3D are explanatory views showing a process for producing the sensor chip.

FIG. 3A shows a base body 10 before being subjected to the sensor chip producing process. In this embodiment, a base body consisting of an aluminum layer 13 is utilized as the base body 10. Alternatively, a base body comprising a support member, which is constituted of a material (e.g., glass) other than aluminum, and a layer of aluminum or an aluminum alloy, which is overlaid on the support member, may be utilized as the base body 10. Specifically, it is sufficient for the surface layer of the base body 10 to be constituted of a material containing aluminum as the principal constituent, and no limitation is imposed upon the structure of the part of the base body 10 other than the surface layer of the base body 10.

In order for the sensor chip 1 to be produced, firstly, anodic oxidation of the surface of the base body 10 is performed by use of an anodic oxidation processing apparatus. In order for the anodic oxidation of the surface of the base body 10 to be performed, firstly, the base body 10 is secured to a holder and located in an electrolyte, which is contained in a reaction vessel, together with an opposite electrode. The electrolyte may be an acidic electrolyte, such as oxalic acid, phosphoric acid, sulfuric acid, or chromic acid. Alternatively, the electrolyte may be a mixture of at least two kinds of acidic solutions.

Thereafter, a voltage of approximately 40V is applied across the base body 10 and the opposite electrode. At the time of the application of the voltage, the base body 10 is connected to a positive terminal side of an electric power source, and the opposite electrode is connected to a negative terminal side of the electric power source. When the voltage is applied across the base body 10 and the opposite electrode, an oxide film is firstly formed on the surface of the base body 10. Also, with the dissolving effect of the acid, fine pits (fine holes) are formed in the surface of the oxide film. Further, as the anodic oxidation progresses, certain pits among the pits described above grow preferentially, and a plurality of pits are thus arrayed at approximately equal intervals in the surface of the oxide film. An area of the oxide film, at which a pit has been formed, is exerted to an electric field, which is stronger than the electric field applied to the other areas of the oxide film. Therefore, the dissolution of the area of the oxide film, at which the pit has been formed, is promoted. As a result, the pit grows in the direction approximately normal to the surface of the aluminum. An area surrounding the pit remains without being dissolved. Alumina obtained with the anodic oxidation has a feature in that naturally formed fine holes are arrayed with markedly high regularity in the alumina.

Figure 3B:
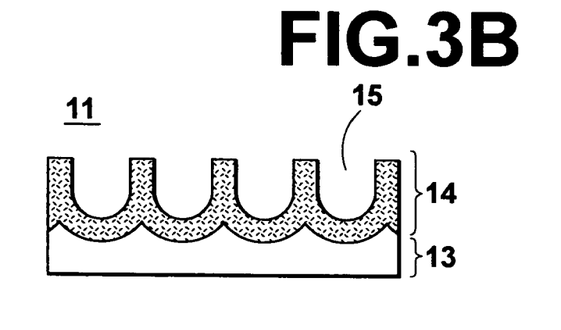

FIG. 3B shows a base body 11 having the surface, on which an alumina layer 14 having a plurality of fine holes 15, 15, . . . has been formed with the anodic oxidation processing. As illustrated in FIG. 3B, the fine holes 15, 15, . . . are arrayed regularly over approximately the entire area of the surface of the base body 11. The hole diameters, the depths, and the intervals of the fine holes 15, 15, . . . vary in accordance with conditions for the anodic oxidation (e.g., the concentration and the temperature of the electrolyte utilized for the anodic oxidation, the technique for the voltage application, the voltage value, and time). Ordinarily, the formation of the fine holes 15, 15, . . . is capable of being controlled accurately such that the period of the fine holes 15, 15, . . . may fall within the range of 10 nm to 500 nm, and such that the hole diameters of the fine holes 15, 15, . . . may fall within the range of 5 nm to 400 nm. In this embodiment, the conditions for the anodic oxidation are set such that the hole diameters of the fine holes 15, 15, . . . may be approximately 200 nm, and such that the period of the fine holes 15, 15, . . . may be approximately 200 nm.

Techniques for finely regulating the positions, at which the fine holes are formed, and the hole diameters of the fine holes are disclosed in, for example, Japanese Unexamined Patent Publication Nos. 2001-9800 and 2001-138300. With the disclosed techniques for regulating the positions, at which the fine holes are formed, and the hole diameters of the fine holes, the fine holes having arbitrary hole diameters and arbitrary hole depths are capable of being formed in an array pattern with an arbitrary period of the fine holes. Also, the variation of the hole diameters of the fine holes is capable of being suppressed to be at most 15%.

Thereafter, gold is loaded in each of the fine holes 15, 15, . . . , which have been naturally formed with the anodic oxidation processing, with a vacuum evaporation technique, a sputtering technique, an electro-plating technique, or the like. In cases where the electro-plating technique is employed, it is necessary that the bottoms of the fine holes 15, 15, . . . have electrical conductivity. In order for the bottoms of the fine holes 15, 15, . . . to have the electrical conductivity, for example, the conditions for the anodic oxidation processing may be adjusted such that the alumina layer at the bottoms of the fine holes 15, 15, . . . becomes markedly thin. Alternatively, the anodic oxidation processing may be iterated a plurality of times, and the alumina layer at the bottoms of the fine holes 15, 15, . . . may thus be rendered thin. As another alternative, the alumina layer at the bottoms of the fine holes 15, 15, . . . may be removed with an etching technique.

Figure 3C:
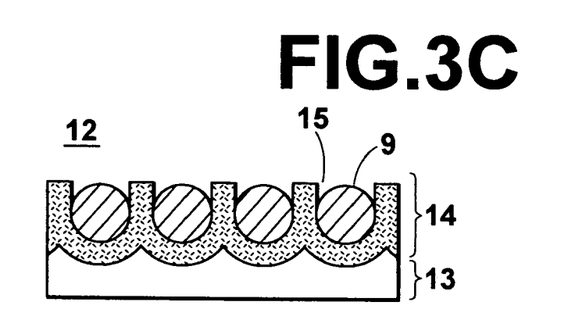

The gold loading processing is finished at the time at which gold has been loaded up to the position identical with the position of the surface of the base body 11. Alternatively, the gold loading processing may be finished before gold is loaded up to the position identical with the position of the surface of the base body 11. In this manner, as illustrated in FIG. 3C, a structure body 12, in which each of the first fine gold particles 9, 9, . . . has been located in the interior of one of the fine holes 15, 15, . . . , is obtained.

Figure 3D:
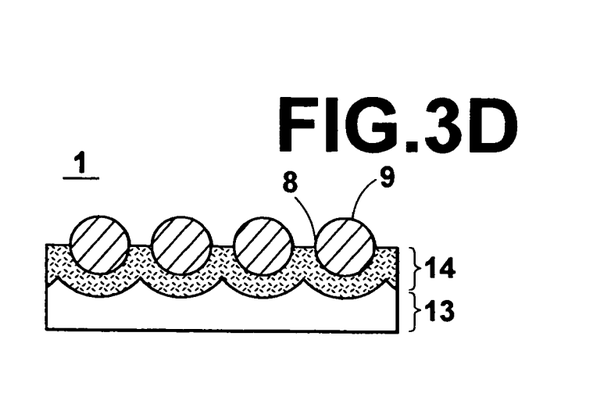

The thus obtained structure body 12 is then subjected to an etching processing, in which an acidic solution capable of selectively dissolving alumina, such as a mixed solution of phosphoric acid and chromic acid, is utilized. With the etching processing, the top layer of the alumina layer 14 at the surface of the structure body 12 is removed. The thickness of the top layer of the alumina layer 14, which top layer is removed, is capable of being adjusted by the etching processing time. Therefore, the etching processing is finished at the time at which apart (e.g., the top half region) of each of the first fine gold particles 9, 9, . . . has been projected from the surface of the structure body 12. In this manner, as illustrated in FIG. 3D, the sensor chip 1 is capable of being obtained.

In this embodiment, gold is employed as the metal loaded in each of the fine holes 8, 8, . . . of the sensor chip 1, i.e. as the material of the fine metal particles. Alternatively, the material of the fine metal particles may be a metal other than gold, e.g. silver, copper, aluminum, nickel, or cobalt. Gold has a high corrosion resistance. Also, the vacuum evaporation processing with gold is capable of being performed at comparatively low temperatures, and therefore the operation for loading gold in each of the fine holes 8, 8, . . . is capable of being performed easily. In cases where silver is employed as the material of the fine metal particles, the sensitivity of the sensor using the sensor chip 1 is capable of being enhanced.

The sensor chip 1 may be produced with a different process. For example, the fine holes may be formed on the surface of the base body by use of a fine processing technique, such as an electron beam irradiation technique, a nano-imprinting technique, or a near field light lithography technique. Thereafter, a metal may be loaded in the fine holes by use of the vacuum evaporation technique, the sputtering technique, the plating technique, or the like. In such cases, the material of the base body need not necessarily be aluminum.

How the test body is detected by use of the sensor chip 1 will be described hereinbelow with reference to FIG. 1. The detection of the test body is performed in the state, in which a sample liquid 3 has been filled in the vessel 2 such that, in cases where the test body is contained in the sample liquid 3, the test body is capable of being adsorbed to the surface of the sensor chip 1. In such cases, a plurality of second fine gold particles are dispersed in the sample liquid 3 and in a state, in which a specific binding substance capable of undergoing specific binding with the test body has been fixed to each of the second fine gold particles. Also, a specific binding substance capable of undergoing specific binding with the test body is previously fixed to the head region of each of the first fine gold particles 9, 9, . . . of the sensor chip 1. In cases where the test body is an antigen, the specific binding substance capable of undergoing specific binding with the test body may be an antibody. Examples of the combinations of the antigen and the antibody include a combination of streptoavidin and biotin, and the like. The kind of the specific binding substance to be fixed to each of the first fine gold particles 9, 9, . . . and the kind of the specific binding substance to be fixed to each of the second fine gold particles vary in accordance with the kind of the test body.

Figure 4:
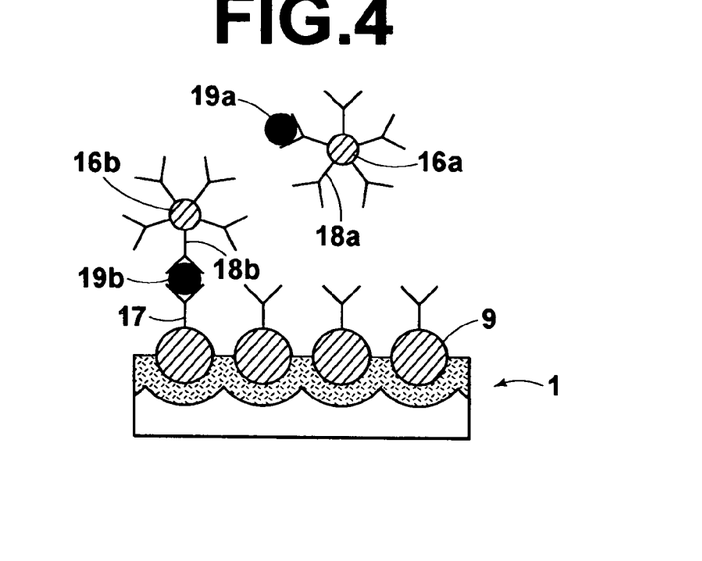
FIG. 4 is a conceptual side view showing how specific binding occurs at a surface of the sensor chip in cases where a test body is contained in a sample liquid.

FIG. 4 is a conceptual side view showing how specific binding occurs at the surface of the sensor chip 1 in cases where the test body is contained in the sample liquid 3. FIG. 4 shows part of the cross-section of the sensor chip 1. As described above, the plurality of the second fine gold particles have been dispersed in the sample liquid 3 and in the state, in which the specific binding substance capable of undergoing specific binding with the test body has been fixed to each of the second fine gold particles. The specific binding substance, which has been fixed to each of the second fine gold particles, undergoes specific binding with the test body, which is contained in the sample liquid 3. As a result, as in the cases of a second fine gold particle 16*a* illustrated in FIG. 4, a plurality of second fine gold particles, each of which has been bound to a test body 19*a* via a specific binding substance 18*a*, are dispersed in the sample liquid 3.

The test body 19*a*, which has been specifically bound to the specific binding substance 18*a* having been fixed to the second fine gold particle 16*a* dispersed in the sample liquid 3, is also specifically bound to a specific binding substance 17, which has been fixed to one of the first fine gold particles 9, 9, . . . of the sensor chip 1. In cases where the two specific bindings occur with one test body, as in the cases of a test body 19*b* illustrated in FIG. 4, the test body is sandwiched between one of the first fine gold particles 9, 9, . . . of the sensor chip 1 and a second fine gold particle 16*b* dispersed in the sample liquid 3. In this state, the first fine gold particle 9 and the second fine gold particle 16*b* are located markedly close to each other.

As illustrated in FIG. 1, the light is irradiated from the white light source 5 through the transparent window 4 and to the sensor chip 1. The light is reflected from the surface of the sensor chip 1. The reflected light is detected by the spectrophotometer 6. The spectrophotometer 6 spectrophotometrically detects the reflected light and forms the spectrum of the reflected light. The thus formed spectrum is outputted to a displaying screen (not shown) or a printer (not shown).

As in the cases of the test body 19*b* illustrated in FIG. 4, in cases where the test body has been adsorbed to the surface of the sensor chip 1 such that the test body is sandwiched between the two kinds of the fine gold particles, i.e. between the first fine gold particle 9 and the second fine gold particle 16*b*, the resonance wavelength of the localized plasmon resonance shifts due to the close location of the first fine gold particle 9 and the second fine gold particle 16*b*. Therefore, in accordance with the variation of the spectrum of the reflected light, the test body contained in the sample liquid 3 is capable of being detected.

With the aforesaid embodiment of the method of detecting a test body in accordance with the present invention, it has been confirmed that the resonance wavelength variation, which is approximately 10 times as large as the resonance wavelength variation found in cases where the second fine gold particles 16*a* and 16*b* are not contained in the sample liquid 3, occurs. Specifically, in cases where the second fine gold particles 16*a* and 16*b* are not contained in the sample liquid 3, the resonance wavelength shifts by several nanometers. However, with the aforesaid embodiment of the method of detecting a test body in accordance with the present invention, wherein the second fine gold particles 16*a* and 16*b* are contained in the sample liquid 3, the resonance wavelength shifts by at least 10 nm. Therefore, with the aforesaid embodiment of the method of detecting a test body in accordance with the present invention, the test body is capable of being detected with a high sensitivity.

In the embodiment described above, the white light is irradiated to the surface of the sensor chip 1, and the light having been reflected from the surface of the sensor chip 1 is spectrophotometrically detected. The spectrum representing the intensity of the reflected light for each of the light wavelengths is thus obtained. Alternatively, monochromatic light having a wavelength corresponding to the resonance wavelength may be irradiated to the surface of the sensor chip 1, and a shift of the resonance wavelength may be detected from a variation of the intensity of the light having been reflected from the surface of the sensor chip 1.

Figure 5:
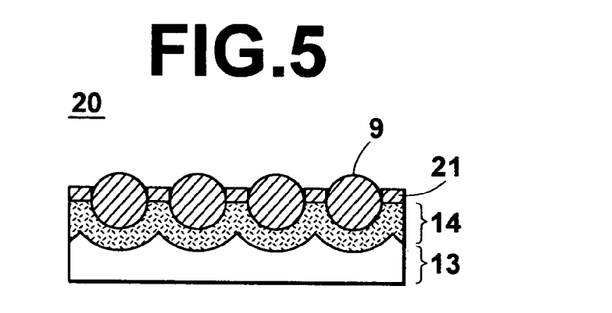
FIG. 5 is a schematic side view showing a different example of a structure of a sensor chip.
Figure 6:
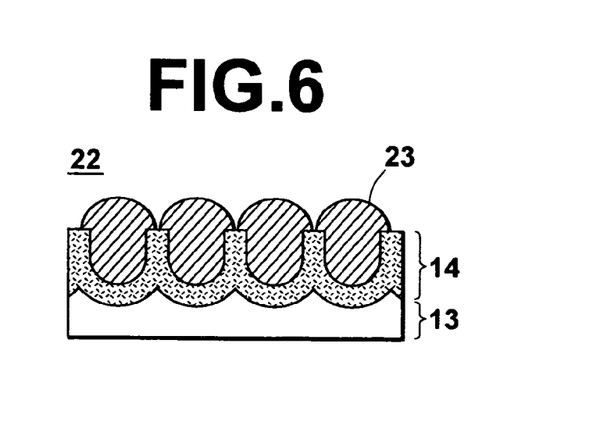
FIG. 6 is a schematic side view showing a further different example of a structure of a sensor chip.

Also, besides the structure of the sensor chip 1, a sensor chip having the structure illustrated in FIG. 5 or FIG. 6 may be employed.

FIG. 5 shows part of the cross-section of a sensor chip 20, which has a structure different from the structure of the sensor chip 1. As illustrated in FIG. 5, as in the cases of the sensor chip 1, the sensor chip 20 h as the structure, in which each of the first fine gold particles 9, 9, . . . is located in one of the fine holes having been distributed and formed in the surface of the base body. The hole diameter of each of the fine holes is equal to approximately 200 nm. The particle diameter of each of the first fine gold particles 9, 9, . . . is equal to approximately 200 nm. The depth of each of the fine holes is approximately 100 nm, i.e. approximately one half of the hole diameter of each of the fine holes. As illustrated in FIG. 5, part (i.e., the head region) of each of the first fine gold particles 9, 9, . . . is projected to the side more upward than the surface of the base body. The sensor chip 20 thus has the structure basically identical with the structure of the sensor chip 1, except that a thin gold film 21 is formed on the areas of the surface of the base body, which areas are located around each of the fine holes of the base body.

By way of example, the sensor chip 20 may be produced in the manner described below. Specifically, the aluminum base body is subjected to the anodic oxidation, and the alumina layer 14 is formed on the aluminum layer 13. Also, gold is loaded in each of the fine holes of the alumina layer 14, and each of the first fine gold particles 9, 9, . . . is thus formed in each of the fine holes of the alumina layer 14. Thereafter, the top layer of the alumina layer 14 is removed with the etching processing. Further, the thin gold film 21 is formed with the vacuum evaporation technique, the sputtering technique, or the like. Alternatively, as in the cases of the sensor chip 1, the sensor chip 20 may be produced with one of other techniques or by use of a different material.

With the structure of the sensor chip 20, near field light, which occurs when the light is irradiated to an area of the first fine gold particles 9, 9, . . . , interacts with the thin gold film 21, and an absorption spectrum due to electric multipoles occurs. Further, due to the synergistic effects of the localized plasmon resonance and the electric multipoles, the variation of the reflected light with respect to a variation of the refractive index of the medium, which is present around the first fine gold particles 9, 9, . . . , becomes markedly sharp. Therefore, with the sensor chip 20, the sensing operation is capable of being performed with a sensitivity higher than the sensitivity obtained with the sensor chip 1.

A sensor chip 22 having the structure different from the structure of the sensor chip 1 will be described hereinbelow. FIG. 6 shows part of the cross-section of the sensor chip 22. As in the cases of the sensor chip 1, the sensor chip 22 has the structure, in which each of first fine gold particles is located in one of the fine holes having been distributed and formed in the surface of the base body. The sensor chip 22 thus has the structure basically identical with the structure of the sensor chip 1, except that the shape of each of fine gold particles 23, 23, . . . is different from the shape of each of the first fine gold particles 9, 9, . . . of the sensor chip 1. As illustrated in FIG. 6, each of the fine gold particles 23, 23, . . . of the sensor chip 22 has a mushroom-like shape such that the diameter of the head region of each of the fine gold particles 23, 23, . . . is larger than the hole diameter of each of the fine holes of the base body.

By way of example, the sensor chip 22 may be produced in the manner described below. Specifically, the aluminum base body is subjected to the anodic oxidation, and the alumina layer 14 is formed on the aluminum layer 13. Also, gold is plated in excess on each of the fine holes of the alumina layer 14. Ordinarily, in the gold loading process for the production of the sensor chip 1, or the like, the plating time is adjusted such that gold may not be deposited beyond the surface of the base body, or excessively deposited gold is removed. However, at the time of the production of the sensor chip 22, the plating time is adjusted such that gold may be plated beyond the surface of the base body. In this manner, as illustrated in FIG. 6, the fine gold particles 23, 23, . . . having the head regions, each of which has the diameter larger than the hole diameter of the fine holes of the base body, are capable of being formed in the fine holes of the base body. Alternatively, as in the cases of the sensor chip 1, the sensor chip 22 may be produced with one of other techniques or by use of a different material.

With the structure of the sensor chip 22, the head regions of the fine gold particles 23, 23, . . . are located close to one another. In cases where the light is irradiated to the fine gold particles 23, 23, . . . , a strong electric field occurs at the space between the adjacent fine gold particles 23, 23, and the reflected light is enhanced by the effect of the electric field. Therefore, the sensing operation is capable of being performed with a sensitivity higher than the sensitivity with the sensor chip 1.

The detection of the test body by use of the reflection type of the sensor is performed in the manner described above. How the detection of the test body is performed by use of a transmission type of sensor for measuring the intensity of the light having passed through a sensor chip will be described hereinbelow.

Figure 7:
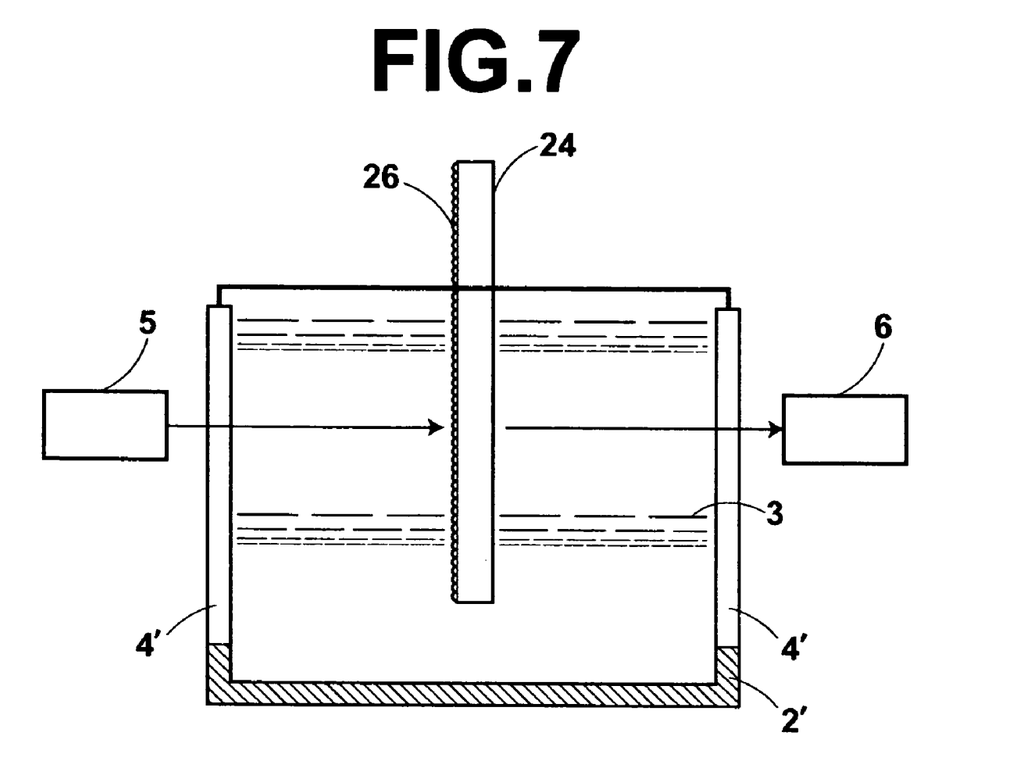
FIG. 7 is a schematic side view showing a transmission type of sensor, which is employed for detection of a test body in a different embodiment of the method of detecting a test body in accordance with the present invention.

FIG. 7 shows a sensor for detecting a test body through measurement of the intensity of light having passed through a sensor chip. As illustrated in FIG. 7, the sensor comprises a vessel 2' provided with transparent windows 4', 4' at opposite sides. The sensor also comprises a sensor chip 24, which is located at the middle of the vessel 2' and in parallel with the transparent windows 4', 4'. The sensor further comprises the white light source 5, which is located on the side outward from the vessel 2'. The sensor still further comprises the spectrophotometer 6, which is located on the side outward from the vessel 2'. A plurality of first fine gold particles 26, 26, . . . are located on the surface of the sensor chip 24, which surface is to be exposed to the light.

The white light source 5 is located at the position such that the white light source 5 is capable of irradiating the white light through the transparent window 41, which stands facing the white light source 5, and to the surface of the sensor chip 24, on which surface the first fine gold particles 26, 26, . . . are located. Also, the spectrophotometer 6 is located at the position that is capable of receiving the light, which has passed through the sensor chip 24. The spectrophotometer 6 spectrophotometrically detects the light, which has passed through the sensor chip 24. The spectrophotometer 6 thus obtains the spectrum and detects the variation of the resonance wavelength.

Figure 8:
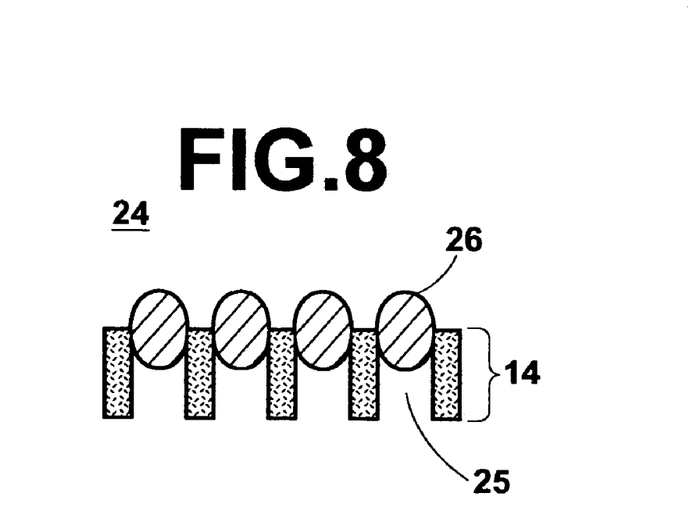
FIG. 8 is a schematic side view showing an example of a structure of a sensor chip for the transmission type of sensor.

FIG. 8 shows part of the cross-section of the sensor chip 24. As illustrated in FIG. 8, the sensor chip 24 has the structure, in which each of the first fine gold particles 26, 26, . . . is located in one of fine holes 25, 25, . . . having been distributed and formed in the surface of the base body. The sensor chip 24 thus has the structure basically identical with the structure of the sensor chip 1, except that each of the fine holes 25, 25, . . . is a through-hole. The hole diameter of each of the fine holes 25, 25, . . . is approximately 200 nm. The particle diameter of each of the first fine gold particles 26, 26, . . . is slightly smaller than the hole diameter of each of the fine holes 25, 25, . . . . As illustrated in FIG. 8, part (i.e., the head region) of each of the first fine gold particles 26, 26, . . . is projected to the side more upward than the surface of the base body.

By way of example, the sensor chip 24 may be produced in the manner described below. Specifically, the aluminum base body is subjected to the anodic oxidation, and the alumina layer 14 is formed on the aluminum layer. Also, gold is loaded in each of the fine holes of the alumina layer 14. Thereafter, the top layer of the alumina layer 14 is removed with the etching processing. Further, the aluminum layer and the alumina layer at the bottoms of the fine holes are removed with the etching processing. Alternatively, as in the cases of the sensor chip 1, the sensor chip 24 may be produced with one of other techniques or by use of a different material.

As illustrated in FIG. 7, the detection of the test body by use of the sensor chip 24 is performed in the state, in which the sample liquid 3 has been filled in the vessel 2' such that, in cases where the test body is contained in the sample liquid 3, the test body is capable of being adsorbed to the surface of the sensor chip 24. In such cases, a plurality of second fine gold particles are dispersed in the sample liquid 3 and in a state, in which a specific binding substance capable of undergoing specific binding with the test body has been fixed to each of the second fine gold particles. Also, a specific binding substance capable of undergoing specific binding with the test body is previously fixed to the head region of each of the first fine gold particles 26, 26, . . . of the sensor chip 24.

Further, the light is irradiated from the white light source 5 through the transparent window 4' and to the sensor chip 24. The light passes through the areas of the first fine gold particles 26, 26, . . . of the sensor chip 24. The light, which has passed through the areas of the first fine gold particles 26, 26, . . . of the sensor chip 24, is detected by the spectrophotometer 6. The spectrophotometer 6 spectrophotometrically detects the light and forms the spectrum of the light. The thus formed spectrum is outputted to a displaying screen (not shown) or a printer (not shown).

In cases where the transmission type of the sensor is utilized, the sensor chip 24 illustrated in FIG. 8, which has the structure such that the head region of each of the first fine gold particles 26, 26, . . . is projected to the side more upward than the surface of the base body, is employed. Also, the sensor chip 24 is located in the sample liquid 3 such that, as illustrated in FIG. 4, the test body is capable of being bound to the second fine gold particles, which are dispersed in the sample liquid 3. In such cases, as in cases where the reflection type of the sensor is utilized, the test body is sandwiched between the two kinds of the fine gold particles, i.e. between the first fine gold particle 26 and the second fine gold particle, and the resonance wavelength of the localized plasmon resonance varies markedly due to the close location of the first fine gold particle 26 and the second fine gold particle.

In the embodiments described above, the particle diameter of each of the first fine metal particles is approximately 200 nm. However, in the method of detecting a test body in accordance with the present invention, it is sufficient for the particle diameter of each of the first fine metal particles to be of a size such that the localized plasmon resonance is capable of being induced, and the particle diameter of each of the first fine metal particles is not limited to the size employed in the embodiments described above. In order for the localized plasmon resonance to be induced, it is necessary that the particle diameter of each of the first fine metal particles be smaller than the wavelengths of the light. Therefore, the particle diameter of each of the first fine metal particles should preferably be at most 200 nm. However, depending upon the wavelengths of the light, the localized plasmon resonance is capable of being induced in cases where the particle diameter of each of the first fine metal particles is slightly larger than 200 nm. The method of detecting a test body in accordance with the present invention also embraces in its scope the cases where the particle diameter of each of the first fine metal particles is slightly larger than 200 nm.

Also, in the embodiments described above, the depth of each of the fine holes of the base body is set to be 100 nm, such that the upper half part of each of the first fine metal particles having the particle diameters of 200 nm may be projected to the side more upward than the surface of the base body. However, the proportion of the projected part of each of the first fine metal particles need not necessarily be equal to one half of each of the first fine metal particles. Alternatively, the proportion of the projected part of each of the first fine metal particles may be larger than one half of each of the first fine metal particles. As another alternative, the proportion of the projected part of each of the first fine metal particles may be smaller than one half of each of the first fine metal particles. However, the proportion of the projected part of each of the first fine metal particles should preferably be as large as possible. In such cases, the close location of the first fine metal particle and second fine metal particle is capable of being obtained easily, and therefore the variation of the resonance wavelength is capable of being found easily.

Further, the shape of each of the first fine metal particles is not limited to the solid sphere-like shape illustrated in FIG. 5, the mushroom-like shape illustrated in FIG. 6, and the ellipsoid-like shape illustrated in FIG. 8. Alternatively, the shape of each of the first fine metal particles may be a circular cylinder-like shape, a rectangular prism-like shape, a circular cone-like shape, or the like. Specifically, each of the first fine metal particles may have one of various shapes, such that the head region of each of the first fine metal particles is projected to the side more upward than the surface of the base body, and such that each of the first fine metal particles is capable of being located close to one of the second fine metal particles having been dispersed in the sample liquid.

As described above, with the method of detecting a test body in accordance with the present invention, both the effect of the state, in which the first fine metal particle on the side of the sensor chip and the second fine metal particle on the side of the test body are located close to each other, and the effect of the state, in which the first fine metal particles having uniform size are arrayed regularly, are capable of being obtained. Therefore, the sensing operation is capable of being performed with a high sensitivity and a high reliability.

What is claimed is:

1. A method of detecting a test body contained in a liquid, comprising the steps of:
   i) obtaining a fine structure body comprising a base body, which has a plurality of fine holes distributed and formed in one surface, and first fine metal particles, each of which has a size such that localized plasmon resonance is capable of being induced, and each of which is located in one of the fine holes of the base body such that a head region of each of the first fine metal particles is projected toward outside the surface of the base body,
   ii) locating the fine structure body in the liquid and in a state, in which a first binding substance capable of specifically binding to the test body has been fixed to the head region of each of the first fine metal particles,
   iii) dispersing a plurality of second fine metal particles, each of which has a size such that the localized plasmon resonance is capable of being induced, in the liquid and in a state, in which a second binding substance capable of specifically binding to the test body has been fixed to each of the second fine metal particles,
   iv) irradiating light to the surface of the fine structure body, where the head regions of the first fine metal particles are projected,
   v) measuring an intensity of the light, which has been reflected from the surface of the fine structure body, or the light, which has passed through the fine structure body,
   vi) outputting the measured intensity of the light in a form visible to a user, and
   vii) detecting the test body, which is contained in the liquid, in accordance with the measured intensity of the light.

2. A method as defined in claim 1 wherein the fine structure body comprises an alumina layer acting as the base body, which alumina layer has been formed with anodic oxidation of a material containing aluminum as a principal constituent, and the first fine metal particles, each of which is located in one of the fine holes of the alumina layer.

3. A method as defined in claim 1 wherein the fine structure body further comprises a thin metal film formed on areas of the surface of the base body, which areas are located around each of the fine holes of the base body.

4. A method as defined in claim 1 wherein a diameter of each of the head regions of the first fine metal particles of the fine structure body is larger than the hole diameter of each of the fine holes of the fine structure body.

5. A method as defined in claim 1 wherein a diameter of each of the head regions of the first fine metal particles of the fine structure body is at most 200 nm.

6. A method as defined in claim 1 wherein a depth of each of the fine holes of the fine structure body is at most 100 nm.

7. A method as defined in claim 1 wherein a variation of hole diameters of the fine holes of the fine structure body is at most 15%.

8. A method as defined in claim 1 wherein the first fine metal particles and/or the second fine metal particles are constituted of a material selected from the group consisting of gold, silver, aluminum, and copper.

9. A method as defined in claim 1, wherein the test body is an antigen and the first and second binding substances are an antibody.

10. A method as defined in claim 3, wherein the thin metal film is formed of gold.

* * * * *